United States Patent [19]

Hussmann

[11] Patent Number: 4,576,820

[45] Date of Patent: Mar. 18, 1986

[54] PROCESS AND APPARATUS FOR FREEING BITTER LUPIN SEED OF BITTER SUBSTANCES THEREIN

[75] Inventor: Peter Hussmann, Florence, Italy

[73] Assignee: Mittex Aktiengesellschaft, Vaduz, Liechtenstein

[21] Appl. No.: 482,335

[22] PCT Filed: Aug. 6, 1982

[86] PCT No.: PCT/EP82/00164

§ 371 Date: Apr. 4, 1983

§ 102(e) Date: Apr. 4, 1983

[87] PCT Pub. No.: WO83/00419

PCT Pub. Date: Feb. 17, 1983

[30] Foreign Application Priority Data

Aug. 6, 1981 [DE] Fed. Rep. of Germany ....... 3131207
Jan. 19, 1982 [DE] Fed. Rep. of Germany ....... 3201378
May 21, 1982 [DE] Fed. Rep. of Germany ....... 3219245

[51] Int. Cl.$^4$ ............................................ A61K 35/78
[52] U.S. Cl. .................................................. 424/195.1
[58] Field of Search ..................... 268/236 J; 424/195, 424/195.1

[56] References Cited

FOREIGN PATENT DOCUMENTS 329201 11/1920 Fed. Rep. of Germany .......... 451/3
350100 3/1922 Fed. Rep. of Germany .
531828 8/1931 Fed. Rep. of Germany .

OTHER PUBLICATIONS

Abstract 8532b, Chemical Abstracts, vol. 43, 1949.
Abstract 56733z, Plant Biochemistry, vol. 76, 1972.
Lehrbuch der pharmazeutischen Technologie, Verlag Chemie, 1979.
Excerpt from Keeler, R. F., Gross, R. (1980) p. 193.
Mittex Brochure, European Search Report.

*Primary Examiner*—Allen J. Robinson
*Assistant Examiner*—John W. Rollins, Jr.
*Attorney, Agent, or Firm*—Schwartz, Jeffery, Schwaab, Mack, Blumenthal & Evans

[57] ABSTRACT

In a process for debittering bitter lupin seed the lupin seed is firstly very finely milled, more specially in a ball mill, and it is then extracted while cold and in counter current with solutions of lupin seed extract with different concentrations in steps, the solvent used being water. The filter cake produced on extraction is dried. After being increased in concentration, the solutions of lupin seed extract are stored and possibly further concentrated. The apparatus for use in the process has in addition to the ball mill a flat bed extractor and a number of storage spaces placed in circuit with each other and with the extractor, such spaces being used to take up the solutions of lupin seed extract. The debittered lupin seed is a high-quality nutrient for man and animals whose protein and fat levels are almost equal to the levels in the lupin seed before debittering, while the concentrate of the lupin extracts containing the bitter substances have a strong plant growth promoting effect, and may be used against many plant pests and for pharmacological purposes.

8 Claims, 1 Drawing Figure

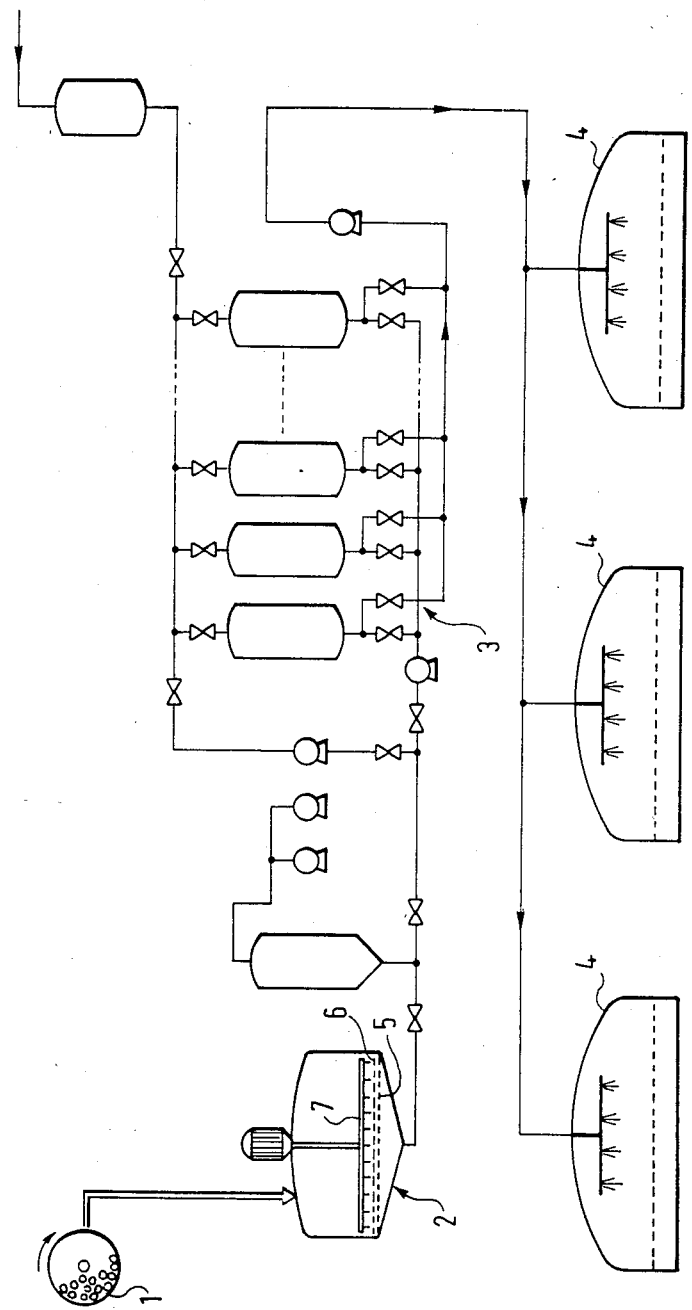

PROCESS AND APPARATUS FOR FREEING BITTER LUPIN SEED OF BITTER SUBSTANCES THEREIN

BACKGROUND OF THE INVENTION

The present invention is with respect to a process and apparatus for debittering bitter lupin seed.

The bitter lupin is a crop plant that has been grown even in ancient Egypt and then later all over the Mediterranean Region and in South America. On account of the high content in its seed of completely digestible protein of 40% and over and its oil content of 15 to 20%, it was and is esteemed as a nutrient for man and animals.

However before bitter lupin seed may be used as a food for man or animals it has to be freed of its bitter substances, this being not only for freeing it of the bitter taste but furthermore to make certain that the bitter substances are not the cause of the so-called lupin disease, that is specially likely in the case of domestic animals.

In one well-known process for freeing lupin seed of bitter substances, the lupin seed is firstly boiled and then steeped in water for up to 48 hours. The shortcoming of this process is that it is complex and high in price to undertake and that there is a marked loss in the food value of the lupin seed. Furthermore large amounts of water are needed and contamination of the rivers or the like into which the waste is run may well be a cause of trouble. There are futhermore debittering processes run on solvents other than water, but such processes have serious shortcomings.

In addition to the use of bitter lupin seed as a food for man and a feedstuff for animals, the seed has futhermore been used in a milled form as a material for promoting the growth of plants. The effects of milled lupin seed on the growth of plants are however small.

SUMMARY OF THE INVENTION

The purpose of the present invention is that of designing a debittering process for lupin seed, which may be undertaken with only a small amount of energy while at the same time generally keeping the nutritive value of the lupin seed unchanged and opening up a way of recovering the bitter substances for further use.

This purpose of the present invention is effected in that the lupin seed is very finely milled and is extracted while cold with lupin extract solutions of different strength in countercurrent, the solvent used being water.

DETAILED DESCRIPTION OF PREFERRED EMBODIMENTS

The useful effect offered by the process of the invention is that while only using water as a solvent and without the input of heat, a debittering extraction operation is undertaken, that on the one hand does not make for any loss in the quality of the protein content of the lupin seed and on the other hand keeps the loss in quality of the nutrients within tight limits, such loss in any case being limited to the so-called nitrogen-free extracts.

Because in the process of the invention the alkaloids present in the lupin seed are recovered in a concentrated form together with substances occurring with them, and may be put to some use, the small loss in the nutrient value may be readily balanced economically. In fact it may even be outweighed, because, as has been seen from tests, the concentrates of the extracts in a liquid or dry form are highly effective materials for promoting plant growth and furthermore may be used as an insecticide and herbicide and for pharmacological purposes.

The apparatus for undertaking the process of the invention is characterized by a milling unit, at least one extraction unit with a filtering lower plate or stage for taking up the lupin seed to be debittered and with storage spaces, put in circuit with the extraction apparatus, for taking up the lupin seed extract solutions.

The useful effect given by this apparatus is that it is of such a design that it may be used in industry, and when run continuously, large amounts of debittered lupin seed may be produced for food and animal feedstuff purposes, while at the same time large amounts of the very valuable lupin extract, containing the bitter substances, are produced that may be put to many different uses, more specially in agriculture and forestry.

Further details and useful effects of the invention will be seen from the detailed account now to be given of the process of the invention and of the apparatus for use in connection therewith, that, together with drying unit for the lupin seed extract produced, will be seen in the figure in the form of a circuit schematic.

The main parts of the apparatus for undertaking the process in keeping with the invention to be seen in the figure are a ball mill 1, a flat bed filter extractor 2 and a number of storage vessels 3 put in circuit with each other and with the extractor 2. In addition to these basic elements the apparatus has parts that are well known to those trained in the art, such as valves, pumps, separators and storage units, that are to be seen in the figure without any account of them being given in the specification. A further part of the apparatus for undertaking the process of the invention in the figure is a drying apparatus having a number of drying housings 4, that is used for drying the extract of alkaloids and substances occurring therewith, as produced by extracting the lupin seed. The extractor 2 has a lower filter plate or stage, that is made up of a grating 5 and a piece of filter fabric 6 thereon made of very fine mesh material. The filter fabric is a monofilament fabric of synthetic resin such as polypropylene, a polyester or polyamide. It is on the lower plate of the extractor that separation of the extraction solutions from the very finely milled solids is undertaken by vacuum.

The extractor 2 furthermore has an agitator 7, that is part of a system that may be moved up and down and furthermore has an apparatus for smoothing over the filter cake formed on the stage of the filter, it futher being used for lifting the filter cake clear of the lower stage of the filter and for cleaning the filter fabric.

In place of a ball mill it is possible to have another form of mill, although a ball mill is preferred because of its very good milling properties. A further point is that in place of a single extractor it would be possible to have a number of them joined together by piping and in come cases it would be possible to do without the bank of vessels, if the extract solutions are able to be stored in the extractors themselves and in the piping joining same together. The time of storing the separate amounts of solution is cut down by increasing the number of extractors.

An account will now be given of the process in keeping with the present invention. A certain amount of unhulled lupin seed to be extracted is mixed with water or a lupin extract solution made up of water and extracted materials containing bitter substances, as produced in an earlier process stages, in a ratio of 1:4 to 1:10 or more specially 1:5 to 1:6, and the mixture so produced is run into the ball mill 1, in which the materials are milled for 2 to 12 hours or for a shorter time. The effect of the miling is that the lupin seed (which may have been broken down somewhat beforehand) may now be milled without any dust so that the lupin seed has a size in a range of 1 micron to 50 microns. Because of this very fine milling of the lupin seed the cellulose is digested, this being very important if one is to get a high nutritional value of the debittered lupin seed.

After milling the lupin seed it is extracted in the extractor 2. The milled lupin seed, turned into a slurry by the wet milling operation, is placed on the stage of the filter in the extractor 2 as a layer with a height of 5 to 50 mm and more specially 10 to 25 mm and is then washed in steps in counter current with amounts of extract solution as produced beforehand, made up of water and extracted materials containing bitter substances from lupin seed and then last washed with pure water, as for example distilled water.

A more detailed account of the extraction process will now be given. The lupin seed extract solutions stored in the storage vessels 3 are mixed in the order of decreasing concentration separately and one after the other with the extraction mass (made up of milled lupin seed and lupin extract solution) and then let off therefrom, the operation being started with the extract solution having the highest concentration and ending with the extract solution with the lowest concentration. At the end pure solvent, in the present example water, is mixed with the more or less completely spent extraction mass and run off therefrom as a weak solution. In this process the concentration of every solution goes up to a value equal to the value had by the solution, supplied in the step coming directly before, before mixing with the extraction mass. The solutions, each becoming more concentrated in the extractor, are run back (after going through the extractor) into that storage container, in which a solution with the concentration in question had so far been stored. The solution produced with the highest concentration after extracting an amount of milled lupin seed is run off into the drying housings 4 for drying and its place taken by new solvent. The spent extraction mass is taken from the extractor 2 and its place taken by newly milled lupin seed. After this a further extraction operation takes place on the same lines. All stages of the extraction process are undertaken without the supply of heat.

For producing the lupin extract solutions of differing concentration, water is mixed at the start of the process with a new batch of very finely milled lupin seed so that a solution is produced that is pumped off from the extraction mass again with a smooth decrease in the concentration thereof. This solution, becoming smoothly or gradually lower and lower in its concentration, undergoes division into a number of amounts of different concentration and is stored in the vessels 3. Next the spent extraction mass has its place taken by a new batch of very finely milled lupin seed and the amounts of solution are mixed, one after the other, with material to be extracted (made up of the very finely milled lupin seed) and then run off therefrom, the concentration of each amount of solution being stepped up to the concentration of the amount of solution last mixed with the material to be extracted before said last-named solution contacted said mass. It is in this way that the concentration figures of the separate amounts of extract solution are increased step by step in the vessels 3 till the desired concentration gradient has been produced in the solutions.

Once the concentration gradient of the solutions has been produced, the process may be undertaken continuously, it only being necessary for the extracted lupin seed to have its place taken after each cycle, bearing in mind the fact that at the end of each cycle the extracting of the lupin seed has to take place with pure or distilled water, this being in view of the two purposes of the process: on the one hand debittering the lupin seed as far as possible and on the other the concentration and production of the bitter substances and substances occurring therewith in the lupin seed.

For full extraction of the lupin seeds it is important to keep to certain values for the heights of the layers of extraction mass and of the filter cake produced by pumping off the extract solution in the extractor. Because at the start of every extracting operation the extraction mass on the filter in the extractor is to be in a layer with a height of 5 to 50 mm and more specially 10 to 25 mm, the filter cake (while still wet) produced in the extraction apparatus at the end of every extracting operation is to be in the form of a layer with a height in a range of some millimeters to 30 millimeters at the most or more specially 5 to 15 mm. Such a height of the wet filter cake is equal to a height of the filter cake when in the dry condition of 2.5 to 6 mm or a weight of 2 to 5 kg/sq. meter.

At the end of the extracting operation there is then a drying operation for drying the filter cake and freeing it of the rest of the water therein. The drying of the filter cake may be done by heating and driving out the water in the form of steam or by expressing the water. Whenever the way used, a useful effect is produced if the amount of water still present in the filter cake at the end of extracting operation is as low as possible. To make certain that this is so, the degree of vacuum used for drawing off the extractant liquid is increased in steps. By continuously smoothing over the cracks formed in the filter cake when drawing off liquid, it is possible to get a filter cake with only 40 to 50% water therein at the end of the extraction operation, that is to say, the amount of water to be extracted from the filter cake on drying is roughly equal to the weight of dry matter.

The drying of the filter cake may take place in the extractor itself by supplying heat artificially thereto or the filter cake may be dried in the sun. Furthermore, the filter cake may be dried outside the extractor using artificial or natural heat, or the rest of the liquid in the filter cake may be expressed as noted earlier. The dried debittered lupin seed product so produced is a high quality foodstuff and animal feed, in which the level of the bitter substances still present therein has been decreased to 0.002%, whereas the levels of protein and fat are generally the same as in the lupin seed before debittering.

The lupin seed extract with the bitter substances, that has a level of dry matter equal to 10 to 30% and more specially 20 to 25%, and furthermore has carbohydrates, fats, proteins and small amounts of minerals in addition to the water-soluble alkaloids, is dried as noted earlier, possibly after being concentrated further beforehand. For drying the extract it is placed in a current of dehumidified air or in an inert gas current at a low temperature, that is to say under 30° C., while supported on a support (that lets the air through) in the drying housings 4 of the drying apparatus.

The dry product produced in this way is a high-value material with many uses, more specially in agriculture and forestry. When used in the form of a dilute solution in water having a concentration of 0.2 to 5% based on dry matter, or in the form of a powder, it is responsible for greatly increasing the rate of growth and the size of the plants. Dependent on the sort of crop, the yields may be increased by 5 to 30% by using the lupin seed extract. When put on at the right rate, that may be readily worked out by simple testing, the lupin seed extract containing bitter substances has a powerful effect against many plant pests.

The debittering process of the present invention may be used for producing oil from lupin seed whatever the process (if any) used before or thereafter.

The use of the process of the invention before another process does however give a useful effect inasfar as the filter cake produced may be granulated, this making the production of oil much simpler.

I claim:

1. A process for debittering particulate starting material comprised of bitter lupin seed, said material containing extractable bitter substances, comprising the steps of:
    (a) providing a series of separate extract solutions, each solution of said series having a differing concentration of said bitter substances, said series having at least a highest-, a second highest-, and a lowest-concentration extract solution;
    (b) providing a filter medium comprised of a layer of said particulate starting material, which filter medium is contacted by said highest-concentration extract solution in said series;
    (c) sequentially contacting said layer with each extract solution of the remaining extract solutions in said series, respectively, in a predetermined order of decreasing concentration of said bitter substances;
    (d) after step (c), contacting said layer with pure water;
    (e) removing said highest-concentration extract solution from said series, so that said second highest-concentration extract becomes the highest-concentration extract solution in said series; and
    (f) repeating steps (b) through (e) at least once,
    wherein (i) said starting material is comprised of bitter lupin seed which was milled beforehand to a particle size in the range of about 1 to about 50 microns, (ii) said layer of said particulate starting material is between about 5 and about 50 mm in thickness, (iii) said highest-concentration extract solution contains a percentage of dry mass between about 10 and 30%, and (iv) said steps (b), (c) and (d) are carried out at a temperature of about 30° C. or less.

2. A process as claimed in claim 1, wherein said milling of said bitter lupin seed comprises a wet milling operation.

3. A process as claimed in claim 2, wherein said wet milling operation comprises using a solution of bitter lupin seed extract in said milling.

4. A process as claimed in claim 1 for obtaining a lupin seed extract containing said bitter substances.

5. A process as claimed in claim 1, further comprising after step (d) the step of dehydrating said highest-concentration extract solution at a temperature below about 30° C.

6. A process as claimed in claim 5, wherein said highest-concentration extract solution is separated from said filter medium by an application of vacuum.

7. A process as claimed in claim 1, further comprising after step (e) the step of drying said layer of particulate starting material to produce a nutrient material comprised of debittered lupin seed.

8. A process for debittering particulate starting material comprised of bitter lupin seed, said material containing extractable bitter substances, comprising the steps of:
    (a) providing a series of separate extract solutions, each solution of said series having a differing concentration of said bitter substances, said series having at least a highest-, a second highest-, and a lowest-concentration extract solution;
    (b) providing a filter medium comprised of a layer of said particulate starting material, which filter medium is contacted by said highest-concentration extract solution in said series;
    (c) sequentially contacting said layer with each extract solution of the remaining extract solutions in said series, respectively, in a predetermined order of decreasing concentration of said bitter substances;
    (d) after step (c), contacting said layer with pure water;
    (e) removing said highest-concentration extract solution from said series, so that said second highest-concentration extract becomes the highest-concentration extract solution in said series;
    (f) dehydrating said highest-concentration extract solution at a temperature below about 30° C.; and
    (g) repeating steps (b) through (e) at least once,
    wherein (i) said starting material is comprised of bitter lupin seed which was milled beforehand to a particle size in the range of about 1 to about 50 microns, (ii) said layer of said particulate starting material is between about 5 and about 50 mm in thickness, (iii) said steps (b), (c) and (d) are carried out at a temperature of about 30° C. or less, and (iv) said highest-concentration extract solution contains a percentage of dry mass between about 10 and 30%.

* * * * *